United States Patent [19]

Ohms et al.

[11] Patent Number: 4,997,536

[45] Date of Patent: Mar. 5, 1991

[54] CONTROL OF ELECTROKINETIC POTENTIAL BY TREATMENT WITH REDOX AGENTS

[75] Inventors: Jack I. Ohms, Palo Alto; James C. Osborne, Jr., Sunnyvale, both of Calif.

[73] Assignee: Beckman Instruments, Inc., Fullerton, Calif.

[21] Appl. No.: 215,834

[22] Filed: Jul. 6, 1988

[51] Int. Cl.$^5$ .............................................. G01N 27/26
[52] U.S. Cl. ............................. 204/180.1; 204/182.2; 204/182.8; 204/183.3; 204/299 R; 210/635; 210/656
[58] Field of Search ............. 204/180.1, 183.3, 299 R, 204/182.8, 182.2; 210/635, 656

[56] References Cited

U.S. PATENT DOCUMENTS

| | | | |
|---|---|---|---|
| 3,909,380 | 9/1975 | Day et al. | 204/180.1 |
| 4,680,201 | 7/1987 | Hjerten | 427/230 |
| 4,690,749 | 9/1987 | Van Alstine et al. | 204/299 R |
| 4,865,706 | 9/1989 | Karger et al. | 204/182.8 |
| 4,865,707 | 8/1989 | Karger et al. | 204/180.1 |

OTHER PUBLICATIONS

T. S. Jayadevaiah, "Semiconductor-Electrolyte Interface Devices for Solar Energy Conversion," *Applied Physics Letters*, vol. 25, No. 7, pp. 399-400, Oct. 1, 1974.
K. D. Legg et al., "n-Type Si-Based Photoelectrochemical Cell . . . ," *Proc. Natl. Acad. Sci. U.S.A.*, vol. 74, No. 10, pp. 4116-4120, Oct. 1977.
M. S. Wrighton, "Surface Functionalization of Electrodes with Molecular Reagents," *Science*, vol. 231, pp. 32-37, Jan. 3, 1986.
H. H. Lauer et al., "Capillary Zone Electrophoresis of Proteins in Untreated Fused Silica Tubing," *Anal. Chem.*, vol. 58, pp. 166-170, 1986.
P. Gozel et al., "Electrokinetic Resolution of Amino Acid Enantiomers . . . ," *Anal. Chem.*, vol. 59, pp. 44-49, 1987.
A. S. Cohen et al., "High-Performance Capillary Electrophoretic Separation of Bases, . . . ," *Anal. Chem.*, vol. 59, pp. 1021-1027, 1987.
A. S. Cohen et al., "High-Performance Sodium Dodecyl Sulfate Polyacrylamide . . . ," *J. of Chromatography*, vol. 397, pp. 409-417, 1987.
A. J. Cunningham et al., "Voltammetric and Chromatographic Monitoring of Neurochemicals in Vivo . . . ," *American Biotechnology Laboratory*, vol. 5, pp. 26-35, Mar./Apr. 1987.
G. Nagy et al., "A New Type of Enzyme Electrode . . . ," *Life Sciences*, vol. 31, No. 23, pp. 2611-2616, 1982.
J. Kohler et al., "Improved Silica-Based Column Packings for High-Performance Liquid Chromatography," *J. of Chromatography*, vol. 385, pp. 125-150, 1987.
J. L. Glajch et al., "Effect of Column Degradation on the Reversed-Phase High-Performance Liquid . . . ," *J. Chromatogrphy*, vol. 384, pp. 81-90, 1987.
S. J. Simko et al., "Quantitative Fast Atom Bombardment Mass Spectrometry of Silylated Silica Surfaces," *Anal. Chem.*, vol 57, pp. 2448-2451, 1985.
F. E. Regnier, "Glycerolpropylsilane Bonded Phases in the Steric Exclusion Chromatography of Biological Macromolecules," *J. of Chromatographic Science*, vol. 14, pp. 316-320, Jul. 1976.

(List continued on next page.)

*Primary Examiner*—T. Tung
*Assistant Examiner*—David G. Ryser
*Attorney, Agent, or Firm*—William H. May; Paul R. Harder; Wen Liu

[57] ABSTRACT

Solid phases such as capillary tubes or solid supports used in chromatography, and in particular electrophoresis, are treated with oxidizing or reducing agents as needed to maintain or restore surface electrical charges or the lack thereof, which become modified during electrophoresis as a result of action by system components in the separation medium or the solutes themselves. The treatment is used as a means of achieving reproducible electroosmotic bulk flow when desired or suppressing unwanted electroosmotic flow arising due to the accumulation of charges on the surface. The result is improved reproducibility of retention times and component separation.

23 Claims, 7 Drawing Sheets

OTHER PUBLICATIONS

J. W. Jorgenson et al., "Capillary Zone Electrophoresis," *Science*, vol. 222, pp. 266-272, Oct. 21, 1983.

C. E. D. Chidsey et al., "Electroactive Polymers and Macromolecular Electronics," *Science*, vol. 321, pp. 25-31, Jan. 3, 1986.

H. W. Werner, "Beam Techniques for the Analysis of Poorly Conducting Materials," *J. Vac. Sci. Technol. A.*, vol. 2, No. 2, pp. 726-731, Apr.-Jun. 1984.

R. Memming, "Anodic Dissolution of Silicon in Hydrofluoric Acid Solutions," *Surface Science*, vol. 4, pp. 109-124, Mar.-Apr. 1966.

Calibiochem product literature.

L. S. Ettre, "Open-Tublular Columns . . . ", *Anal. Chem.*, vol. 57, No. 13, Nov. 1985.

S. H. Chang, "Use of Oxiranes in the Preparation of Bonded Phase Supports," *J. Chromatography*, vol. 120, pp. 321-333, 1976.

R. P. W. Scott, "The silica Gel Surface and its Interactions with Solvent . . . ," *J. Chromatographic Sci.*, vol. 18, pp. 297-306, Jul. 1980.

S. Schomburg, "Stationary Phases in High Performance Liquid Chromatography," *LC-GC*, vol. 6, No. 1, pp. 36-50.

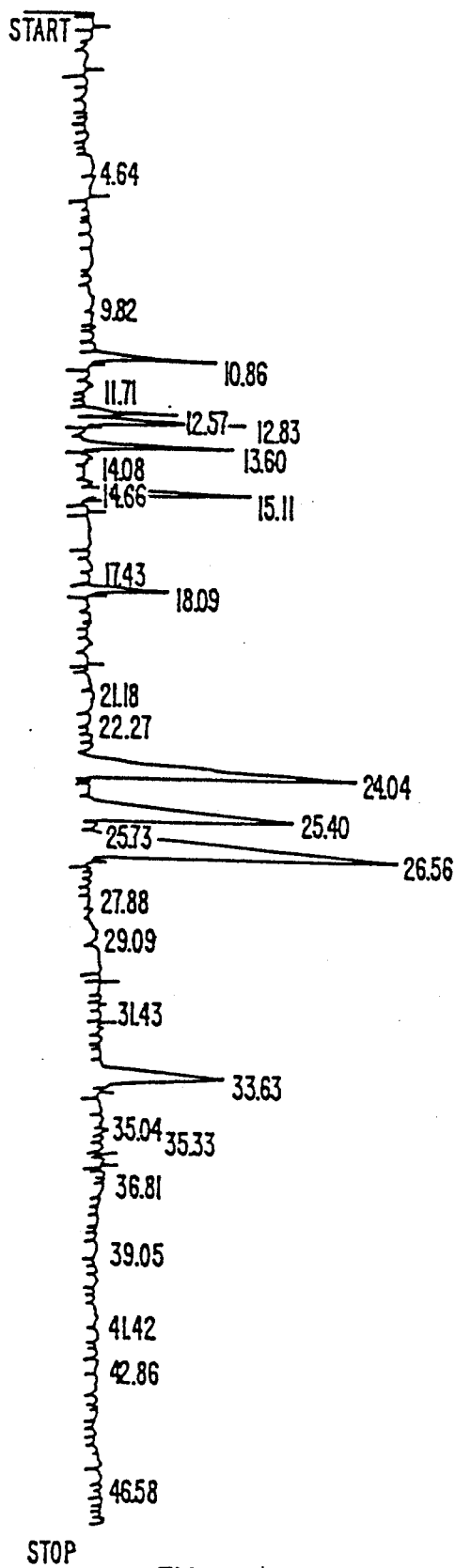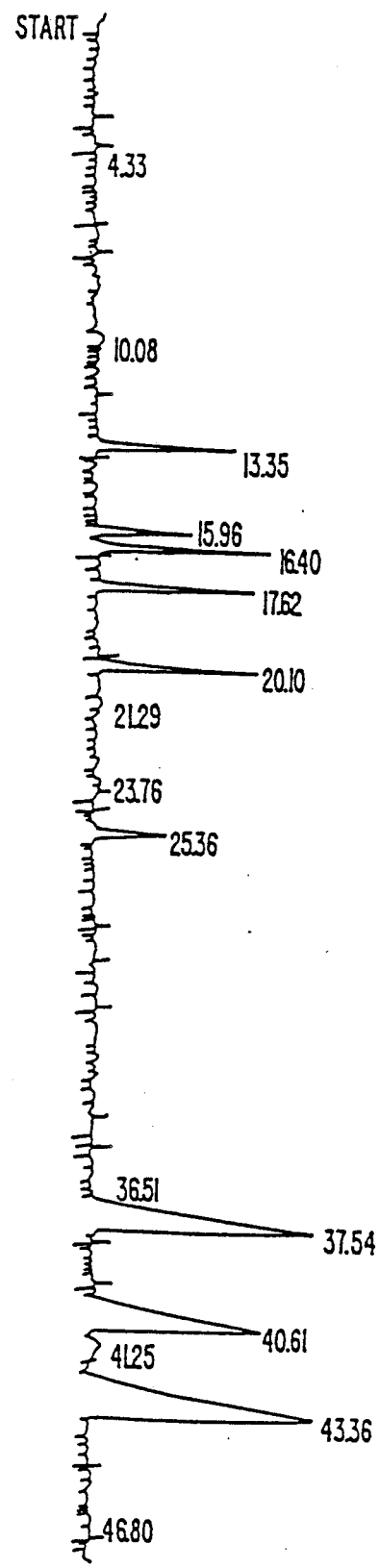
FIG._2.   FIG._1.

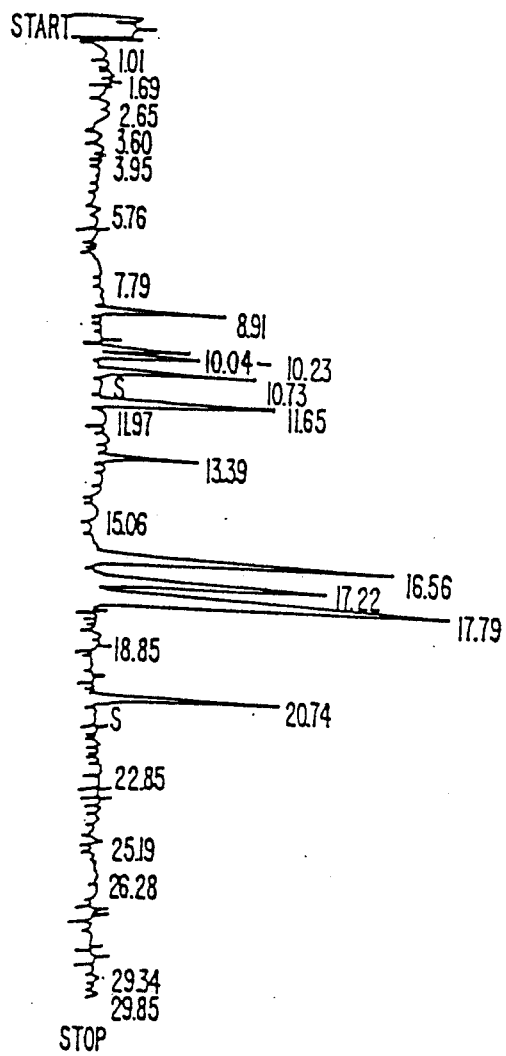
FIG._4.
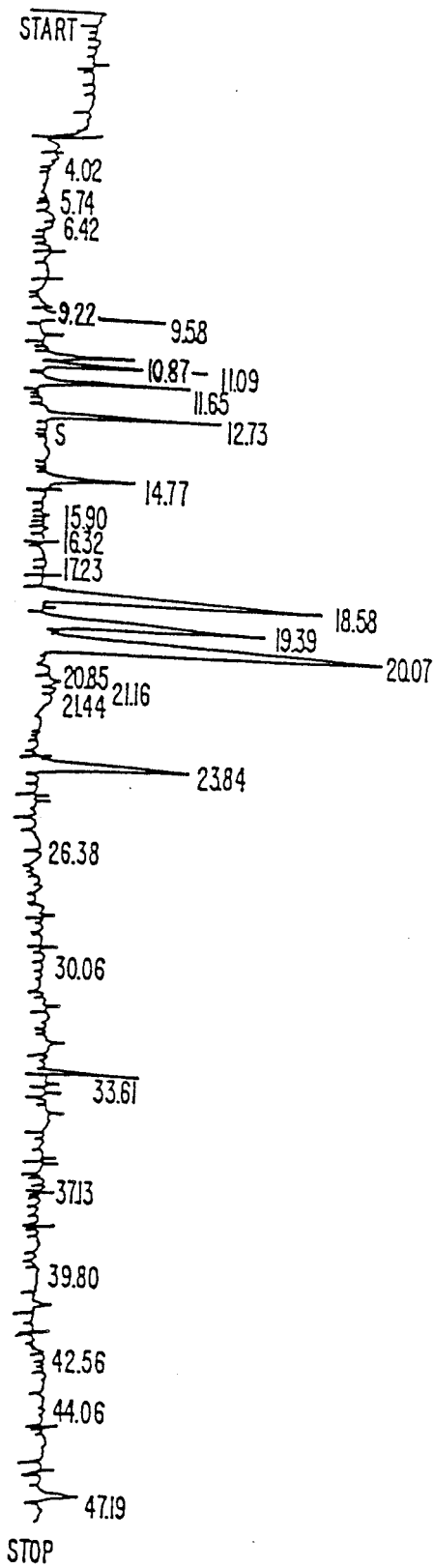
FIG._3.

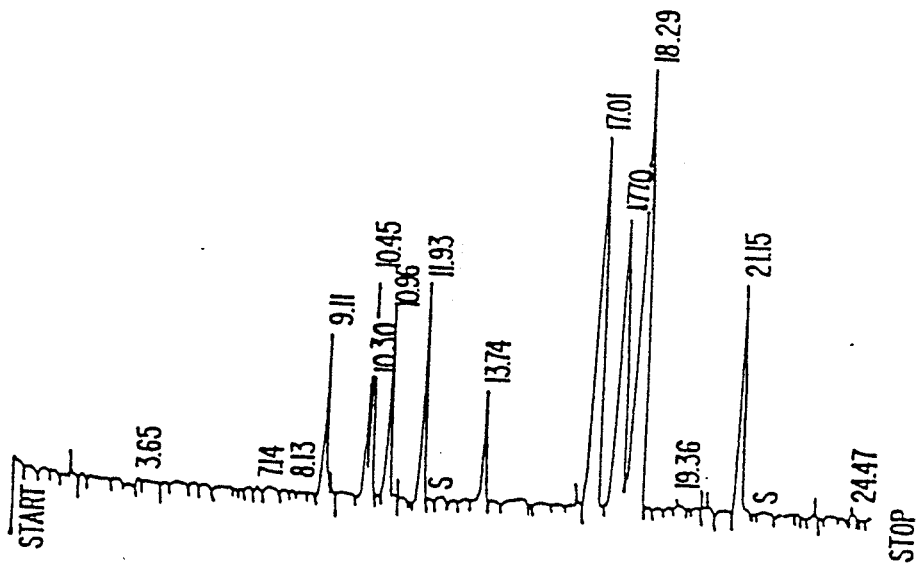
FIG._5.
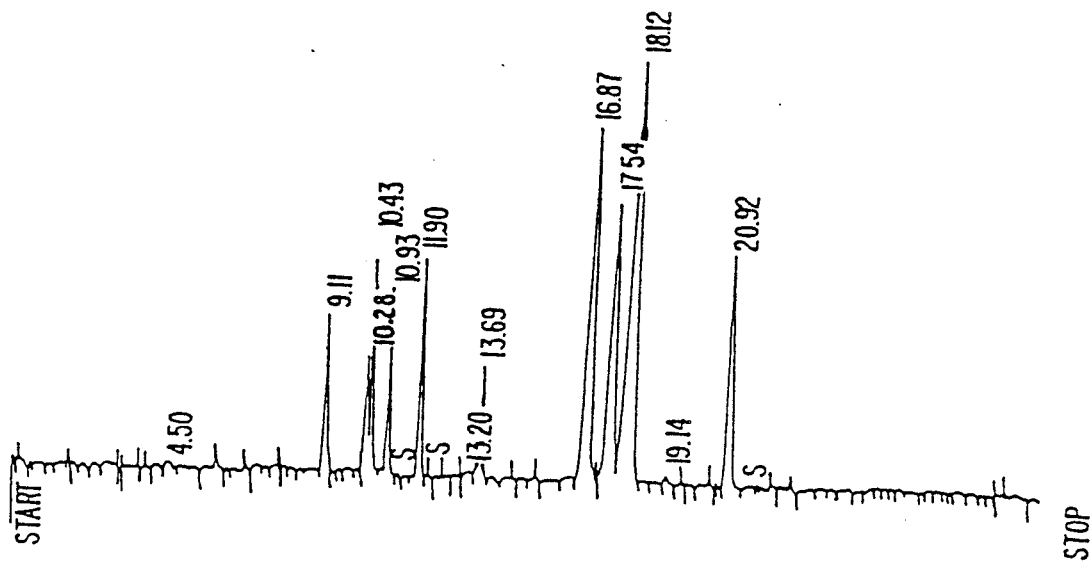
FIG._6.

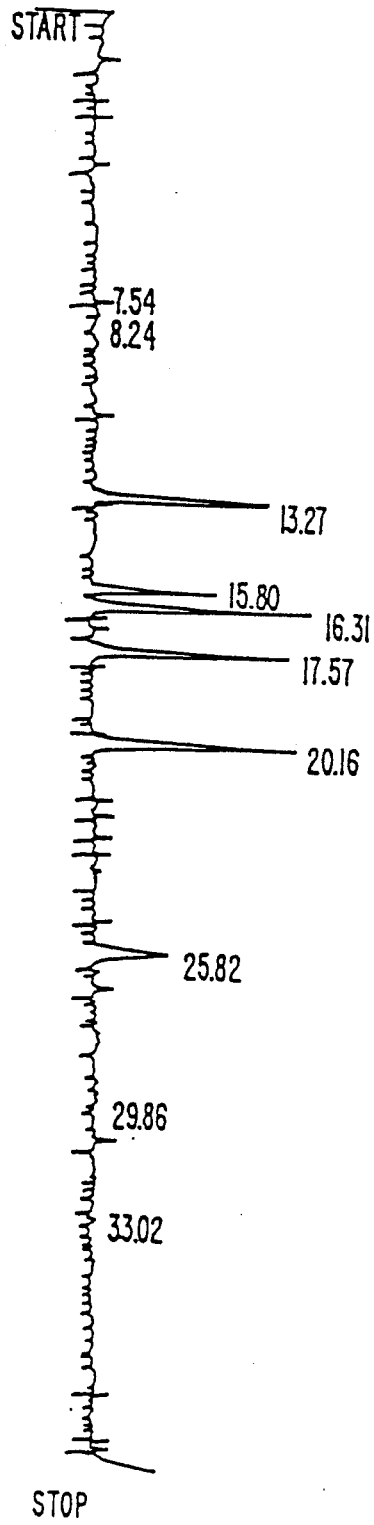
FIG._8.
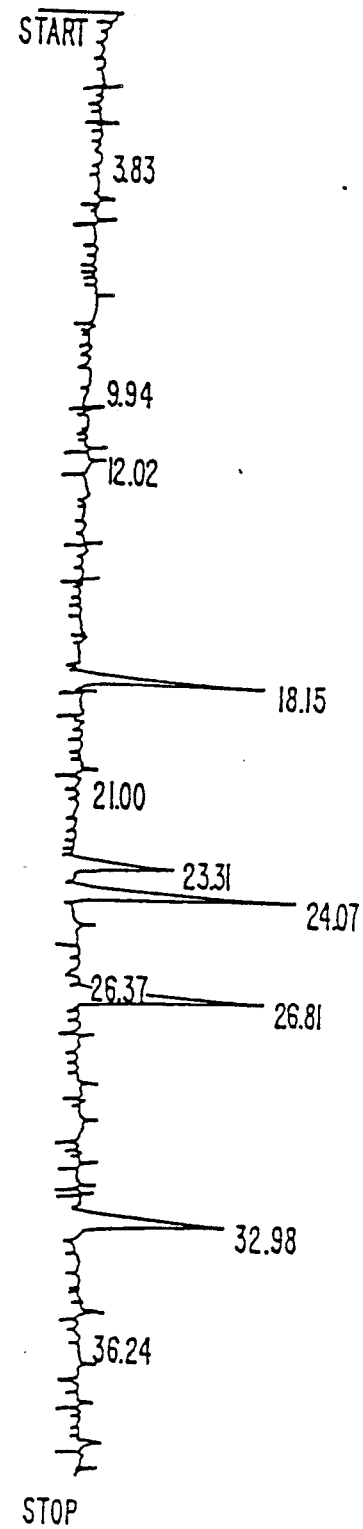
FIG._7.

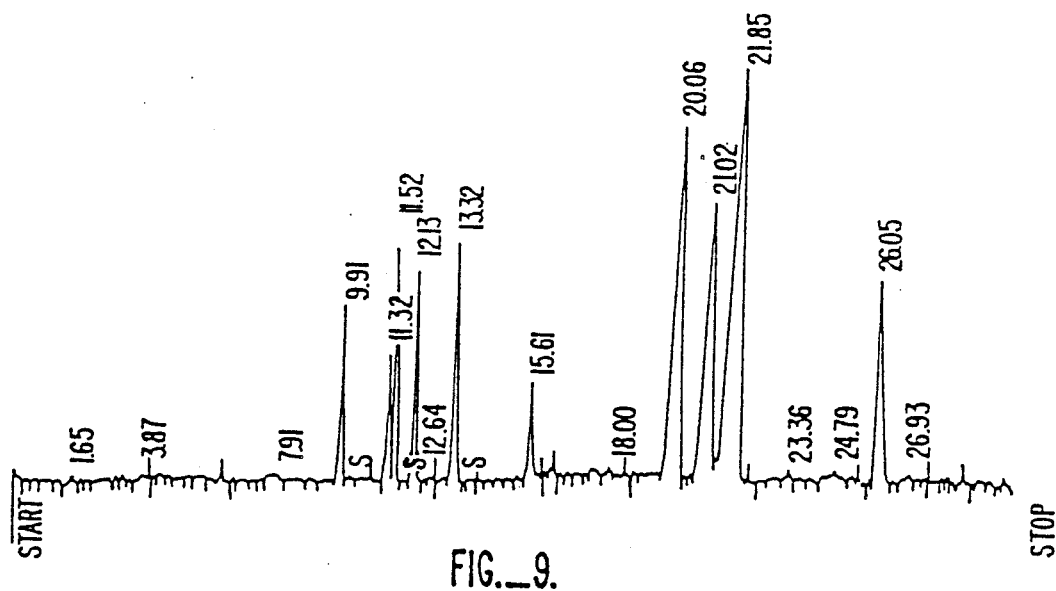
FIG._9.
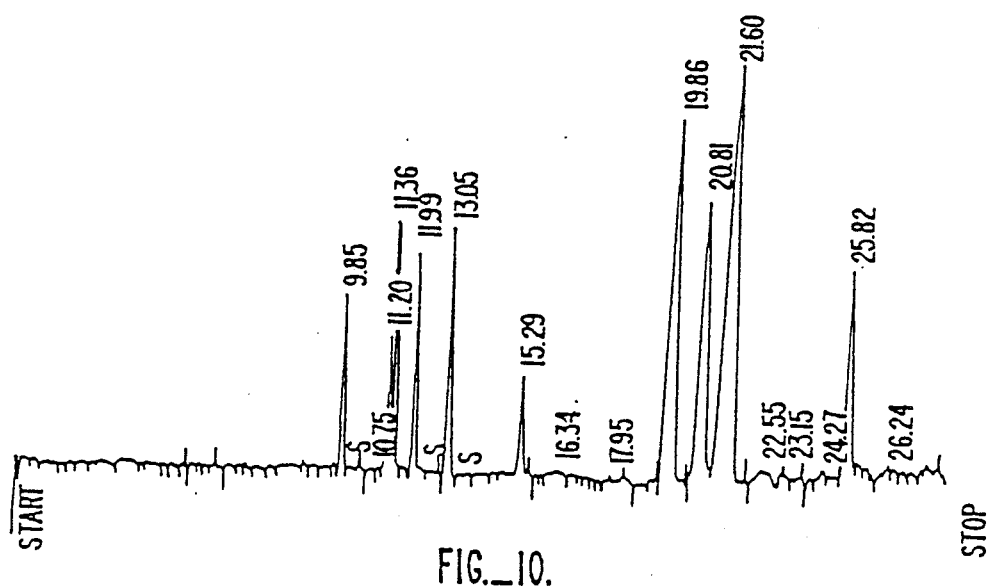
FIG._10.
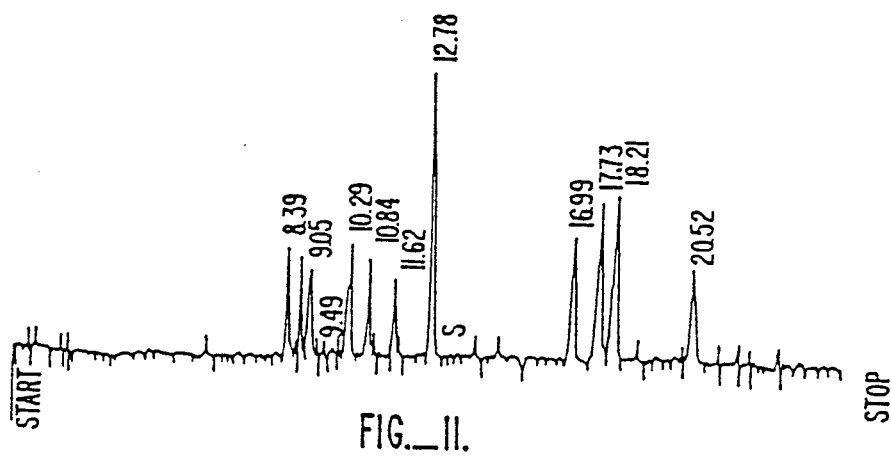
FIG._11.

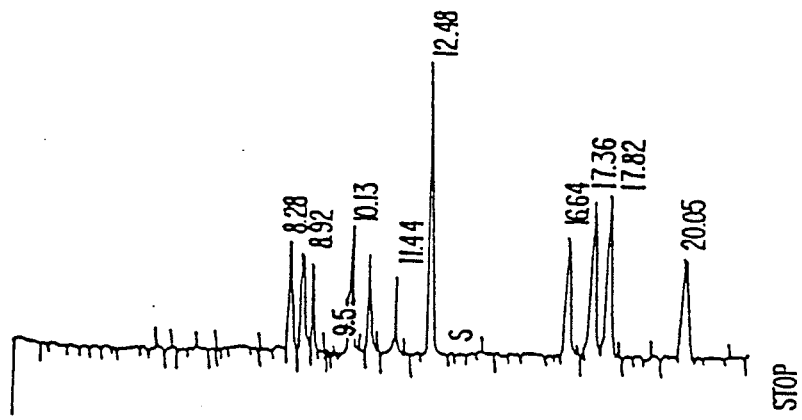
FIG._12.
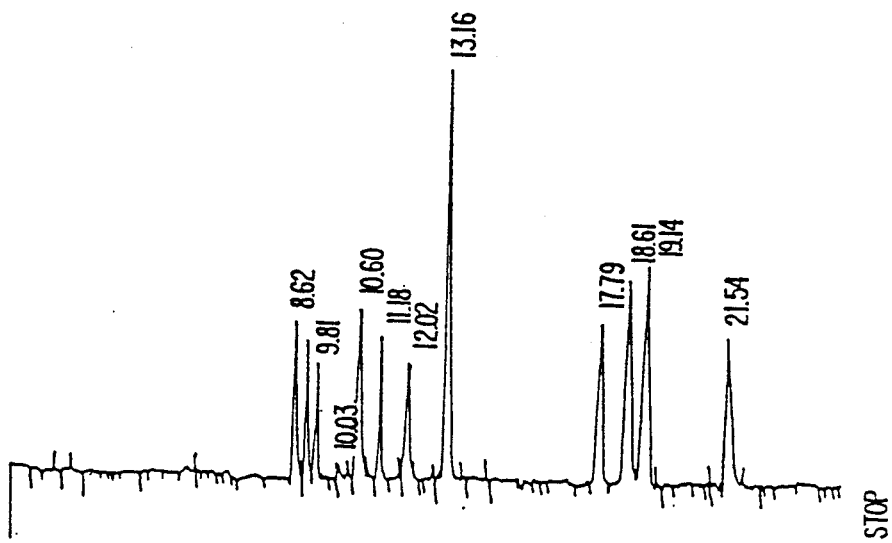
FIG._13.
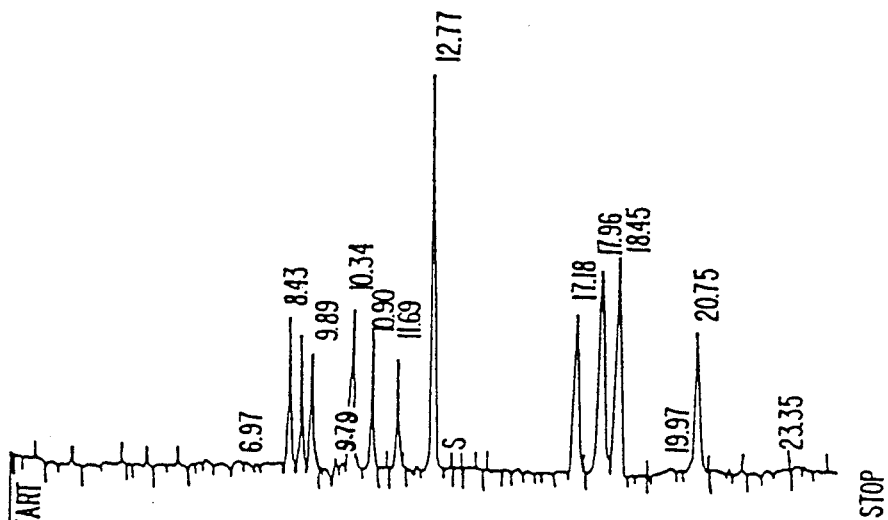
FIG._14.

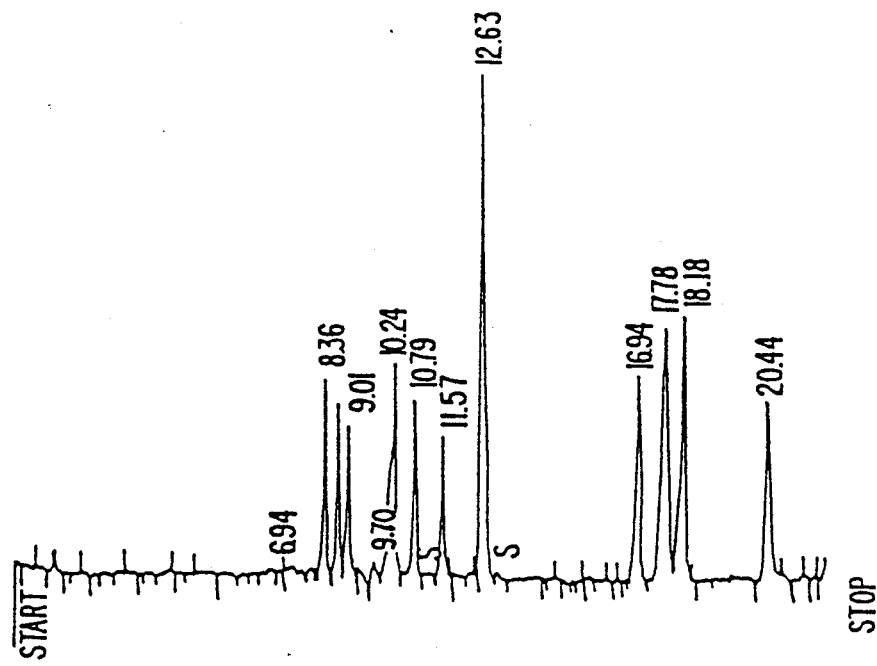
FIG._15.
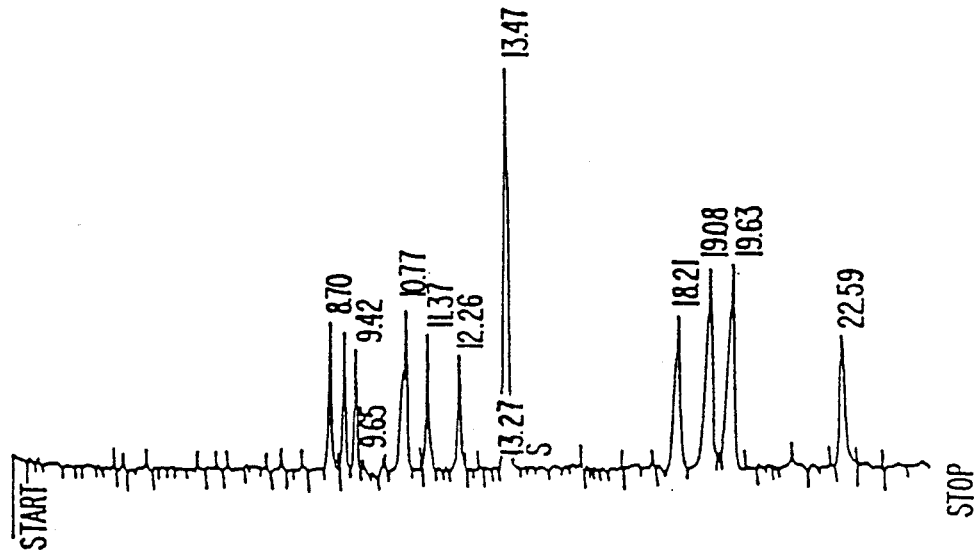
FIG._16.

CONTROL OF ELECTROKINETIC POTENTIAL BY TREATMENT WITH REDOX AGENTS

This invention relates to electrokinetic phenomena, and in particular to solid phases and components used in electrophoresis and chromatography.

BACKGROUND AND SUMMARY OF THE INVENTION

Solid elements are included in electrophoretic and chromatographic systems for a variety of reasons, including their use as sites for the partitioning of solutes and as retaining walls for housing a separation medium. Solid elements may thus take the form of particles, porous or otherwise, capillary tubes, plates to hold a slab, and other configurations. Examples of chromatographic systems using solid elements are affinity chromatography, reversed phase chromatography, ion exchange chromatography size exclusion chromatography and the various forms of electrophoresis including gel electrophoresis, open-tube electrophoresis, isotachophoresis (also referred to as displacement electrophoresis) and isoelectric focusing. In some cases, the solid element plays an active role in the partitioning, and in other cases a passive role. In some cases, the solid element contributes to the bulk flow of solutes through the separation medium through electroendosmosis (also referred to as electroosmotic flow, as it is herein), while in other cases such flow is considered to be an interference.

Each type of separatory system has its own particular utility. Capillary electrophoresis in its various forms, for example, is significant among electrophoretic systems in general due to a number of advantages which it offers. In particular, it is useful in operations where high speed and efficiency are important. This is because its narrow bore columns promote rapid heat dissipation from the column interior to its surroundings. A high voltage may thus be applied without causing excessive Joule heating. Samples having components which separate only under high voltage can thus be partitioned in such tubes. In addition, the small volume of separation medium used in comparison to other electrophoretic systems lends itself to very small sample sizes. The most common types of capillary electrophoresis are gel electrophoresis, isoelectric focusing, isotachophoresis (also referred to as "displacement" electrophoresis) and free zone electrophoresis, with or without electroosmotic bulk flow.

Wall effects are a major consideration in capillary electrophoresis as well as forms of chromatography. In capillary electrophoresis, there is a high ratio of wall surface area to the volume of the separation medium, and high proximity of the wall to the components being partitioned. In some capillary systems, the presence of an electrokinetic potential is relied on to produce an electroosmotic bulk flow as an integral part of the partition mechanism. Other systems rely primarily on electrophoretic mobility. Electroosmotic flow in such systems interferes with the partitioning, and where present it is sought to be suppressed or eliminated. In many separations, a combination of electrophoretic mobility and electroosmotic flow is used at a ratio which is experimentally derived to provide the cleanest and most efficient separation.

The magnitude of the electrokinetic potential in any electrophoretic system, and hence the degree of electroosmotic flow, are dependent on the surface characteristics of the solid element, which is vulnerable to the various materials which come in contact with it during each separation. These include carrier fluids, buffers, partitioning reagents retained with the carrier, and the solutes sought to be separated. Chemical reactions between these substances and the wall of the solid element, as well as entrapment or retention of these substances by the wall, tend to change the electrical characteristics of the wall, thus affecting the electrokinetic potential. These unwanted interactions with the wall also interfere with the partitioning effect which occurs within the bulk of the separation medium. The changes accumulate with repeated runs, resulting in a loss of reproducibility and, in some cases, to a loss of the partitioning effect itself. The loss of reproducibility is a particularly serious problem in automated systems where a series of samples are injected and partitioned automatically in sequence.

It has now been discovered that an electrokinetic potential may be maintained and reproducibility restored in such systems by treatment of the capillary surface with a redox reagent, i.e., a reagent which promotes either reduction or oxidation on species with which it comes into contact. The choice between oxidation and reduction will depend on the effect sought to be achieved, i.e., the surface electrical character sought to be restored.

For instance, we have found that with silica, oxidizing agents decrease the electrokinetic potential whereas reducing agents increase the electrokinetic potential. The effects are accomplished presumably through modification of surface SiOH groups. With electrophoresis, oxidizing agents would be used when the desired driving force is electrophoretic mobility only, and reducing agents would be used when electroendosmotic flow is the desired driving force (or "pump") for the system. The oxidizing or reducing reagent may serve either a restorative function or a maintenance function, depending on whether it is used as a treatment between runs, or added as a system component during the actual separation.

Further advantages and embodiments of the invention will be apparent from the following description.

BRIEF DESCRIPTION OF THE DRAWINGS

The figures attached hereto are traces from a photometric detector for a series of runs in a capillary electrophoresis tube on samples of the same mixture, to show how retention times vary when various treatments are applied both before and during runs. These figures represent the data produced by the runs described in the "EXAMPLES" section below.

DETAILED DESCRIPTION OF THE INVENTION AND PREFERRED EMBODIMENTS

Surfaces to which the redox agent treatment of the invention may be applied are the surfaces of any materials which are susceptible to the formation of an electrokinetic potential and the resulting electrical double layer when placed in contact with a polar solution of an electrolyte. This invention also extends to surfaces which are normally electrically neutral but which are susceptible to oxidation or reduction during use in an electrophoresis separation by species passing through the tube. Capillaries made of silica-containing materials are of particular interest with electrophoretic separations, notably glass, quartz and fused silica. The size of the capillaries is not critical and can vary widely. Electroosmotic flow can occur in tubes ranging from a few microns in diameter to several thousand. Those of most interest for purposes of the present invention will generally fall within the range of about 2 microns to about 500 microns in diameter.

Oxidizing agents which may be used in accordance with the present invention include any of the large number of agents known to those skilled in analytical chemistry, organic synthesis, and biotechnology, preferably those which are soluble in polar solvents such as water. Examples include peroxides permanganates, and chromates. Specific examples within these groups include quaternary ammonium compounds such as benzyltriethylammonium permanganate and bis(benzyltriethylammonium) dichromate, hydrogen peroxide and sodium peroxide. Likewise, a broad range of reducing agents may be used. Examples include metal hydrides boryl hydrides and urates, as well as biochemical reducing agents such as dithiothreitol and dithioerythritol.

Treatment is most conveniently achieved by contacting the reagents in a polar solution with the solid element, either by flushing it with the solution or adding the reagents to the buffer solutions or other solutions used during the actual separation or both. The concentration in the solvent is not critical and may vary widely, although in most cases, concentration ranging from about 25 mM to about 250 mM will provide the best results. Similar concentrations may be used when the reagent is an additive during the separation.

The duration of the treatment will generally be governed by the degree necessary to restore the solid element surface to the desired state. This will depend on the frequency of the treatment, and other predictable parameters such as the concentration of the oxidizing or reducing agent in the treatment solution and the temperature at which the treatment is performed. When treatment is done on a capillary tube, for example, by flushing the capillary between runs, a flush using about 5 to about 50 capillary volumes will generally be effective. The degree in manner of flushing or other methods of contact which will be most appropriate for any given system will be apparent to those skilled in the art.

To add to the effect of the oxidizing or reducing agent, a desorbing agent may also be included in the treatment solution. This will be particularly useful where surface contamination or modification is caused by entrapment or deposition of mobile species during electrophoretic runs. The deposited or entrapped species may be either the solutes sought to be separated in the run or other pollutants present in the solutions. Suitable desorption agents are those which are active in such functions as denaturing the contaminating species, dissociating the species from themselves or from the surface or preventing nonspecific binding in general. Selection of the appropriate desorption agent in any given circumstance will depend on the nature of the sample and species to be separated and their stability or reactivity in the presence of desorption agents of particular types, such as neutral or charged agents, etc. Examples of suitable desorption agents, depending on the system, are urea and guanidine.

The invention is of particular interest to various types of electrophoretic separations occurring in capillary tubes, as stated above. Primary examples include gel electrophoresis, isoelectric focusing isotachophoresis and free zone electrophoresis. Additional components contributing to the overall partitioning effect may be included, in accordance with techniques well known to those skilled in the art. For example, the formation of micelles with sodium dodecyl sulfate may be used to enhance the partitioning effect.

The following examples are offered for purposes of illustration, and are intended neither to define nor limit the invention in any manner.

EXAMPLES

Samples from a mixture of nucleic acid components were repeatedly injected into a fused silica capillary and subjected to electrophoresis with varying pre-run flushes and additives to the electrolyte. Fused silica contains surface hydroxyl groups which are responsible for the electroosmotic effect. The mixture composition at an individual component concentration of $5 \times 10^{-4}$ M was as follows:

Uridine
Uracil
Cytidine
Cytosine
Thymidine
Thymine
2-Azidocytidine
Adenosine
Thymidine monophosphate
Deoxycytidine monophosphate
Cytidine monophosphate
3-Azidothymidine The system parameters were as follows:

| Capillary | fused silica, 77 micron I.D., 69 mm length, 55 cm to detector |
| --- | --- |
| Detection | 260 nm, direct capillary optical path |
| Voltage | 22,500 V |
| Current | 138 µA |
| Temperature | 15° C. |
| Electrolyte | 0.025M phosphate, pH 6.86, 0.2M SDS |
| Sample Injection | 5 to 10 nanoliters |

The variables from run to run were as follows:

| Run No. | Pre-run Flush* | Electrolyte Additive |
| --- | --- | --- |
| 1 | N₂; water; N₂ | none |
| 2 | 0.025M DTE** | none |
| 3 | water | none |
| 4 | 1M urea | none |
| 5 | 0.025M DTE | none |
| 6 | water | none |
| 7 | 0.05M H₂O₂ | none |
| 8 | 0.025M DTE | none |
| 9 | 0.05M DTE | none |
| 10 | 0.05M DTE | 0.05M DTE |
| 11 | 0.10M DTE | 0.10M DTE |
| 12 | none | 0.05M DTE |
| 13 | 0.05M DTE | 0.05M DTE |
| 14 | none | 0.05M DTE |
| 15 | none | 0.05M DTE |
| 16 | none | 0.05M DTE |

*Pre-run flushes were made with 10-20 column volumes.
**DTE denotes dithioerythritol.

Detector traces from these runs are shown in FIGS. 1 through 16. As an indication of the scale of the figures, the first (leftmost) peak in FIG. 1 represents cytidine at a retention time of 13.35 minutes, and the last peak represents azidothymidine (AZT) at a retention time of 43.36 minutes.

What these traces demonstrate is a significant decrease in retention time (representing an increase or restoration of electroosmotic flow) following treatment with DTE. The retention time continued to drop in a roughly asymptotic manner until hydrogen peroxide was used (Run 7). Hydrogen peroxide is an oxidizing agent which removes the hydroxyl groups from the fused silica surface, lessening electroosmotic flow and thereby increasing all retention times. Subsequent restorative flushes with DTE however returned the retention times to essentially the same asymptotic level reached prior to the hydrogen peroxide treatment. The data demonstrate that DTE was effective in both the flushes and in the electrolyte solution during the run itself.

The foregoing is offered primarily for purposes of illustration. It will be readily apparent to those skilled in the art that certain modifications, variations, and substitutions may be made in the materials, procedural steps and operating conditions described herein without departing from the spirit and scope of the invention.

We claim:

1. A method for controlling electrokinetic potential created in the presence of a solid whose surface is susceptible to the formation of an electric charge when it is exposed to an electrolyte, said method comprising treating said solid with a reagent selected from the group consisting of oxidizing agents and reducing agents to achieve a preselected charge distribution on the surface of said solid, wherein the reagent reduces electrokinetic potential if it is an oxidizing agent and the reagent increases electrokinetic potential if it is a reducing agent.

2. A method in accordance with claim 1 in which said solid is a capillary wall.

3. A method in accordance with claim 1 in which said solid is a solid column packing material.

4. A method in accordance with claim 1 in which said solid is a silica-containing solid substance.

5. A method in accordance with claim 1 in which said solid is a member selected from the group consisting of glass, quartz, and fused silica.

6. A method in accordance with claim 1 in which said solid is fused silica and said reagent is a reducing agent.

7. A method in accordance with claim 1 wherein the surface is treated by contacting said solid with a solution of said reagent either prior to, during or prior to and during exposure to the electrolyte.

8. A method for controlling electroosmotic flow occurring during capillary electrophoresis in a capillary whose internal surface is susceptible to the formation of an electrokinetic potential, said method comprising treating said surface with a reagent selected from the group consisting of oxidizing agents and reducing agents to achieve a preselected charge distribution on said surface, wherein the reagent reduces electrokinetic potential if it is an oxidizing agent and the reagent increases electrokinetic potential if it is a reducing agent.

9. A method in accordance with claim 8 wherein the surface is treated prior to said capillary electrophoresis.

10. A method in accordance with claim 8 wherein the surface is treated during said capillary electrophoresis.

11. A method in accordance with claim 8 wherein the surface is treated prior to and during said capillary electrophoresis.

12. A method in accordance with claim 8 in which said capillary is formed of a silica-containing material.

13. A method in accordance with claim 8 in which said capillary is formed of fused silica.

14. A method in accordance with claim 8 in which said reagent is an oxidizing agent.

15. A method in accordance with claim 14 in which said oxidizing agent is a member selected from the group consisting of peroxides, permanganates, and chromates.

16. A method in accordance with claim 8 in which said reagent is a reducing agent.

17. A method in accordance with claim 16 in which said reducing agent is a member selected from the group consisting of metal hydrides, borohydrides, urates, dithiothreitol, and dithioerythritol.

18. A method in accordance with claim 8 in which said reagent is a reducing agent and said surface is treated with a solution of said reducing agent at a concentration ranging from about 25 mM to about 250 mM.

19. A method in accordance with claim 8 further comprising treating said surface with a desorbing agent to promote the desorption of solid adhering to said surface by nonspecific binding.

20. A method in accordance with claim 19 in which said surface is treated with the desorbing agent simultaneously with said reagent.

21. A method in accordance with claim 19 in which said surface is treated with the desorbing agent subsequent to being treated with said reagent.

22. A method in accordance with claim 19 in which said desorbing agent is a member selected from the group consisting of urea and guanidine.

23. A method in accordance with claim 19 in which said desorbing agent is urea.

* * * * *